United States Patent
Porteous et al.

(10) Patent No.: US 10,086,162 B2
(45) Date of Patent: *Oct. 2, 2018

(54) PATIENT NASAL INTERFACE FOR USE WITH A NASAL AIRWAY PRESSURE SYSTEM

(71) Applicant: CareFusion 207, Inc., San Diego, CA (US)

(72) Inventors: Eric Porteous, Corona, CA (US); Brian W. Pierro, Yorba Linda, CA (US); Khalid Said Mansour, Corona, CA (US); Geoff Wise, San Jose, CA (US)

(73) Assignee: CareFusion 207, Inc., San Diego, CA (US)

( * ) Notice: Subject to any disclaimer, the term of this patent is extended or adjusted under 35 U.S.C. 154(b) by 258 days.

This patent is subject to a terminal disclaimer.

(21) Appl. No.: 15/012,679

(22) Filed: Feb. 1, 2016

(65) Prior Publication Data

US 2016/0144145 A1 May 26, 2016

Related U.S. Application Data

(63) Continuation of application No. 13/460,643, filed on Apr. 30, 2012, now Pat. No. 9,259,548.

(51) Int. Cl.
*A61M 16/06* (2006.01)
*A61M 16/00* (2006.01)
*A61M 16/08* (2006.01)

(52) U.S. Cl.
CPC .... *A61M 16/0666* (2013.01); *A61M 16/0057* (2013.01); *A61M 16/0672* (2014.02); *A61M 16/06* (2013.01); *A61M 16/0816* (2013.01)

(58) Field of Classification Search
CPC .. A61M 15/00; A61M 16/00; A61M 16/0069; A61M 16/04; A61M 16/0488;
(Continued)

(56) References Cited

U.S. PATENT DOCUMENTS 3,824,999 A 7/1974 King
5,193,532 A * 3/1993 Moa .................... A61M 16/12
128/204.18

(Continued)

FOREIGN PATENT DOCUMENTS

WO WO-2011062510 A1 5/2011

OTHER PUBLICATIONS

Extended European Search Report for Application No. 13784280.3, dated Nov. 9, 2015, 8 pages.

(Continued)

*Primary Examiner* — Annette Dixon
(74) *Attorney, Agent, or Firm* — McDermott Will & Emery LLP

(57) ABSTRACT

A patient nasal interface is provided that includes a female portion and a first registration feature. The female portion receives a male portion of a generator head. The female portion wraps around and over the male portion when the male portion is inserted into the female portion of the patient nasal interface. The first registration feature is configured for mating with a second registration feature associated with the male portion of the generator head and wherein the mating of the first registration feature with the second registration feature provides a feedback to an operator upon proper insertion of the male portion into the female portion.

20 Claims, 5 Drawing Sheets

(58) Field of Classification Search
CPC .......... A61M 16/0493; A61M 16/0497; A61M 16/06; A61M 16/0616; A61M 16/0622; A61M 16/0633; A61M 16/0638; A61M 16/0666; A61M 16/0672; A61M 16/0677; A61M 16/0683; A61M 16/0694; A61M 16/08; A61M 16/0816; A61M 16/0825; A61M 16/0858; A61M 16/0875; A61M 16/10; A61M 16/1075; A61M 16/109; A61M 16/12; A61M 16/127; A61M 16/16; A61M 16/20; A61M 2005/312; A61M 2039/1027; A61M 2039/1083; A61M 2039/1088; A61M 2206/11; A61M 2210/0618; A61M 2210/0625; A61M 39/105; A61M 39/12; A61M 5/288; A61M 5/31511; A61M 5/348; A62B 18/02; A62B 7/00; A62B 7/02; B05C 17/00506; B05C 17/00516; B05C 17/00579; F16L 37/098; F16L 37/38; F16L 37/56; Y10S 128/26; Y10S 128/911; Y10S 128/912
USPC .......... 128/200.24, 200.26, 202.27, 202.28, 128/203.12, 203.18, 203.22, 204.18, 128/204.21, 204.25, 205.25, 206.11, 128/206.21, 206.23, 206.24, 206.26, 128/206.27, 206.28, 207.11, 207.13, 128/207.14, 207.17, 207.18, 858, 911, 128/912
See application file for complete search history.

(56) References Cited

U.S. PATENT DOCUMENTS

| | | | |
|---|---|---|---|
| 5,755,458 A | 5/1998 | Donovan | |
| 6,804,656 B1 | 10/2004 | Rosenfeld et al. | |
| 7,207,945 B2 | 4/2007 | Bardy | |
| 7,959,574 B2 | 6/2011 | Bardy | |
| 7,987,850 B2 | 8/2011 | Zollinger et al. | |
| 9,259,548 B2 * | 2/2016 | Porteous | A61M 16/0666 |
| 2003/0200970 A1 * | 10/2003 | Stenzler | A61M 16/0666 128/207.18 |
| 2004/0177850 A1 | 9/2004 | Gradon et al. | |
| 2007/0074724 A1 | 4/2007 | Duquette et al. | |
| 2007/0125379 A1 | 6/2007 | Pierro et al. | |
| 2007/0125387 A1 * | 6/2007 | Zollinger | A61M 16/0666 128/207.18 |
| 2007/0272249 A1 | 11/2007 | Chandran et al. | |
| 2007/0277824 A1 | 12/2007 | Aylsworth et al. | |
| 2008/0060657 A1 * | 3/2008 | McAuley | A61M 16/0666 128/207.18 |
| 2008/0276938 A1 | 11/2008 | Jeppesen et al. | |
| 2009/0165799 A1 * | 7/2009 | Duquette | A61M 16/0666 128/204.25 |
| 2010/0108073 A1 | 5/2010 | Zollinger et al. | |
| 2010/0252044 A1 | 10/2010 | Duquette et al. | |
| 2010/0258128 A1 | 10/2010 | Zollinger et al. | |
| 2011/0100364 A1 | 5/2011 | Faram | |
| 2011/0232649 A1 | 9/2011 | Collazo et al. | |
| 2012/0080033 A1 | 4/2012 | Varga et al. | |
| 2012/0080034 A1 | 4/2012 | Mansour et al. | |

OTHER PUBLICATIONS

International Search Report and Written Opinion for Application No. PCT/US2013/036825, dated Jul. 23, 2013.

European Office Action for Application No. 13784280.3, dated Nov. 15, 2017, 4 pages.

* cited by examiner

PATIENT NASAL INTERFACE FOR USE WITH A NASAL AIRWAY PRESSURE SYSTEM

CROSS-REFERENCES TO RELATED APPLICATIONS

This application is a continuation of U.S. patent application Ser. No. 13/460,643, entitled "Patient Nasal Interface for Use with a Nasal Airway Pressure System," filed on Apr. 30, 2012, all of which is hereby incorporated by reference in its entirety for all purposes.

FIELD OF THE INVENTION

The present technology relates generally to nasal interfaces. More particularly, the present technology relates to nasal interfaces for use with a nasal airway pressure system.

BACKGROUND

Airway pressure therapy has been employed for many years to treat patients experiencing respiratory difficulties due to a number of reasons. Airway pressure therapy involves creating or generating a positive airway pressure at a nasal airway pressure system that is delivered to a patient through a patient nasal interface, which interfaces directly or indirectly with the patient's nasal airway via the patient's nostrils.

One example of respiratory difficulties is an infant with under-developed lungs, especially in the case of a premature infant or a neonate. The airway pressure therapy prevents the infant's lungs from collapsing during exhalation and assists in lung expansion during inhalation.

Another example of respiratory difficulties is an individual that has sleep apnea that causes a portion of their air way passage to intermittently collapse while they are sleeping. The airway pressure therapy can be used to prevent the air way passage from collapsing.

There are different types of nasal airway pressure systems. One is continuous positive airway pressure (CPAP) that generates continuous positive airway pressure for the patient. A CPAP that is used with a nasal interface is referred to as a nasal CPAP (nCPAP). Other examples of airway pressure systems include fixed flow, ventilator type systems and variable flow systems.

DRAWINGS

Figure 1:
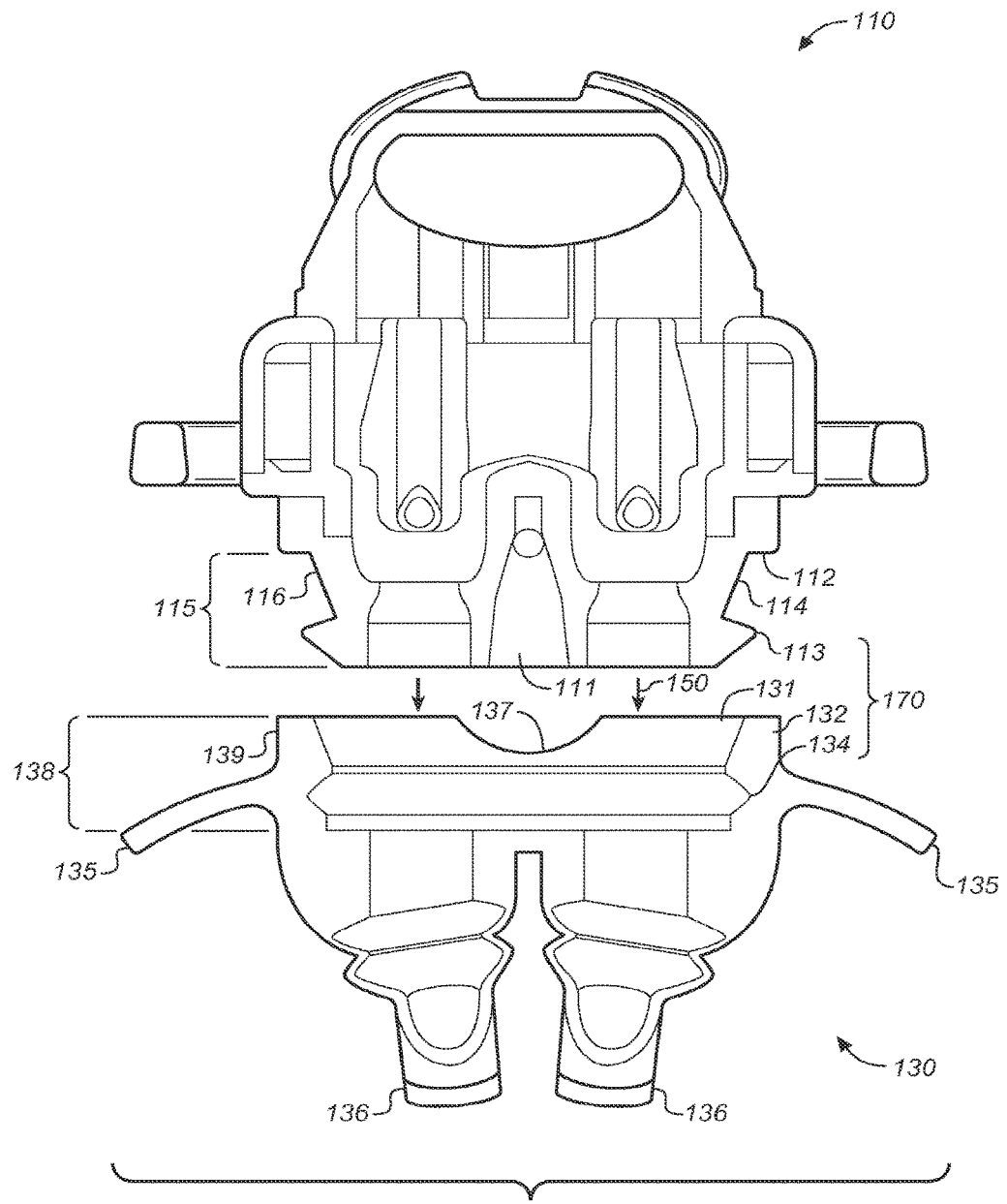
FIG. 1 depicts a vertical cross section view of a generator head and a patient nasal interface, according to one embodiment.

The drawings referred to in this description should not be understood as being drawn to scale unless specifically noted.

DESCRIPTION OF EMBODIMENTS

An airway pressure system that can be used for providing air pressure to a person's nostrils, directly or indirectly, is referred to as a nasal airway pressure system. The nasal airway pressure system generates air pressure that can be delivered through tubes to a generator head, which in turn is coupled to a patient nasal interface. A patient nasal interfaces can be prong type or a mask type, among others. The prong type typically includes two prongs that can be inserted into the patient's nostrils. The mask type is a cup shaped structure that can cover the person's nose.

Typically a patient nasal interface is for single patient use. Typically a patient nasal interface is discarded prior to 14 days of use.

Conventional generator heads and conventional patient nasal interfaces are difficult to couple resulting in leaks through gaps between them. In the event that they are not properly coupled, the nasal airway pressure system would indicate that there is reduced pressure due to a leak. However, with conventional components it is difficult for the operator to determine that the leak is due to a small gap between the generator head and the patient nasal interface. Therefore, operators frequently respond to seeing the reduced pressure by tightening the interface to the patient's face increasing the possibility of skin irritation, skin damage, or discomfort to the patient. Dim lighting, as is frequently found in neonatal intensive care units (NICUs), especially increase the probability of improper insertion and increase the difficulty of determining the cause of the problem when there is a leak.

If there is an occlusion or a leak between the generator head and the patient nasal interface, the patient will not receive the benefit of the positive air pressure generated by the nasal airway pressure system. Achieving a proper seal between the generator head and the patient nasal interface is especially important when the person receiving the therapy is at greater risk, such as a premature infant or an infant with reduced lung capacity.

Therefore, according to various embodiments, a generator head and a patient nasal interface are provided that couple with each other to provide a seal that prevents air from leaking between the generator head and the patient nasal interface. Further, according to various embodiments, a patient nasal interface is provided that includes a female portion that wraps around and over a male portion of a generator head that is inserted into the female portion of the patient nasal interface. Further still, according to various embodiments, respective registration features are associated with the generator head and the patient nasal interface to provide feedback, in the form of an audible noise or a tactile snap, to the person connecting the generator head and the patient nasal interface.

It is frequently difficult to properly align conventional patient nasal interfaces with the generator head. For example, an operator may reverse the patient nasal interface's orientation with respect to the generator head. Cases have been seen where the operator has bent prongs on a prong type interface causing the prongs to dig into the inner walls of the patients nostrils. Further, improper alignment can result in leaks. Therefore, according to one embodiment, an alignment feature is provided to enable an operator to determine that the patient nasal interface is aligned properly with the generator head. According to one embodiment, an interface feature is provided to enable an operator to determine that the patient nasal interface is not aligned properly with the generator head.

Therefore, according to various embodiments, the generator head and the patient nasal interface are provided that are well suited for use in a hospital, in an intensive care unit, a step down facility, in a home, or in a sleep clinic, among others. Various embodiments provide for ease of use in a darkened environment, such as a NICU.

FIG. 1 depicts a vertical cross section view of a generator head and a patient nasal interface, according to one embodiment. The patient nasal interface 130 can be made of silicone or silicone-like material. For example, the patient nasal interface 130, for example, can be made of molded silicon, soft vinyl, or thermoplastic elastomeric, among other things.

The generator head 110, for example, can be made of a plastic that is more rigid than the material that the patient nasal interface 130 is made from. The generator head 110, for example, can be made of a rigid or substantially rigid plastic.

The generator head 110 includes a male portion 115 and a proximal pressure line port 111, among other things, according to one embodiment. The male portion 115 provides a sealing area 116 on the outer surface of the male portion 115. The generator head 110 provides a geometric shape that includes an external mount 113 oriented toward the bottom of the generator head 110 with a notch 114 above the external mount 113 and a lip 112 above the notch 114. As depicted in FIG. 1, the external mount 113 approximates the shape of a triangle that sticks out. However, various embodiments are well suited to other shapes, such as semi circles or a shape that approximate a square, among others. According to one embodiment, the generator head 110's external mount 113 is convex.

The patient nasal interface 130, according to one embodiment, includes a female portion 138, a lip 131, tabs 135 on each side, two prongs 136, and an alignment feature 137. The prongs 136 can be inserted into a patient's nostrils. The female portion 138 includes an internal notch 134, a slanted wall 133 and is oriented toward the base 132 of the patient nasal interface 130. The slanted wall 133, according to one embodiment, has a larger circumference toward the base 132 than toward the internal notch 134. The lip 131 is located along the top of the patient nasal interface 130's base 132. The female portion 138 provides a sealing area 139 on the inner surface of the female portion 138.

As depicted in FIG. 1, the patient nasal interface 130's internal notch 134 approximates a shape of a triangular notch. However, embodiments are well suited to other shapes, such as a semi circular notch, a square or a parallelogram, among other things. According to one embodiment, the patient nasal interface 130's internal notch 134 is concave.

The male portion 115 of the generator head 110 can be inserted into the female portion 138 of the patient nasal interface 130. According to one embodiment, the female portion 138 goes over and wraps around the male portion 115. The female portion 138, according to one embodiment, is made of material that stretches to conform to the male portion 115 upon insertion 150.

The respective sealing areas 116, 139, according to one embodiment, provide respective attachment geometries that can mate with each other. For example, as depicted, the generator head 110's external mount 113 approximates the shape of the patient nasal interface 130's internal notch 134, the generator head 110's notch 114 approximates the shape of the patient nasal interface 130's slanted wall 133, according to one embodiment. The respective external mount 113 and the internal notch 134 are configured to form a radial seal with respect to each other, according to one embodiment. Various embodiments are well suited to other attachment geometries that use shapes that approximate semicircles, squares, or parallelograms, among other things.

The generator head 110 and the patient nasal interface 130 have respective registration features 134, according to one embodiment. For example, as depicted in FIG. 1, the generator head 110 has an external mount 113 and the patient nasal interface 130 has an internal notch 134. Upon proper insertion 150 of the generator head 110's male portion 115 into the patient nasal interface 130's female portion 138, feedback is provided to the operator that performed the insertion 150, according to one embodiment.

For example, the operator may hear or feel a snap when the external mount 113 pops into place inside of the internal notch 134. The sound of the snap is an example of audible feedback and the feel of the snap is an example of tactile feedback. If the operator does not feel or hear the snap, then the operator knows that a proper insertion has not been accomplished and can continue attempts until they feel or hear the snap. This enables the operator to know that they have achieved a proper seal that will prevent air from leaking despite working in darkened rooms, such as neonatal intensive care units (NICUs).

Further, the generator head 110's registration feature 113 can press into the material of the patient nasal interface 130, for example, due to the interface 130's material stretching around the generator head 110's male portion 115.

According to one embodiment, the respective registration features 113, 134 provide a locking detail 170 that significantly reduces the probability of the generator head 110 and patient nasal interface 130 being accidentally decoupled. For example, typically it would take a noticeable amount of effort to move the generator head 110's registration feature 134 out of the patient nasal interface 130's registration feature 134.

Although the locking detail 170 significantly reduces the probability of the generator head 110 and the patient nasal interface 130 being accidentally decoupled, the locking detail 170, according to one embodiment, still enables the operator to remove a patient nasal interface 130 from the generator head 110 and couple the generator head 110 with a different patient nasal interface 130. For example, in order to reduce the probability of skin irritation, skin damage or damage to the nasal septum, the locking detail 170 still allows the operator to intermittently switch between a prong type interface and a mask type interface.

Although FIG. 1 depicts one locking detail 170 provided by the registration features 113, 134 associated with the respective generator head 110 and patient nasal interface 130, various embodiments are well suited for more than one locking detail 170. For example, two registration features may be associated with each of the generator head 110's male portion 115 and the patient nasal interface 130's female portion 138. More specifically, assuming that there are two registration features 114 associated with the generator head 110's male portion 115 and two corresponding registration features 134 associated with the patient nasal interface 130's female portion 138, then the operator may perceive at least two feedbacks, such as two audible snaps or two tactile snaps, or a combination thereof.

The alignment feature 137, for example, has a shape that approximates the shape of the outer surface of the lower side of the proximal pressure line port 111, as will become more evident. Various embodiments are well suited to using other features of the generator head 110 besides the proximal pressure line port 111. As will become more evident, the patient nasal interface 130 can also have an interference feature.

Figure 2:
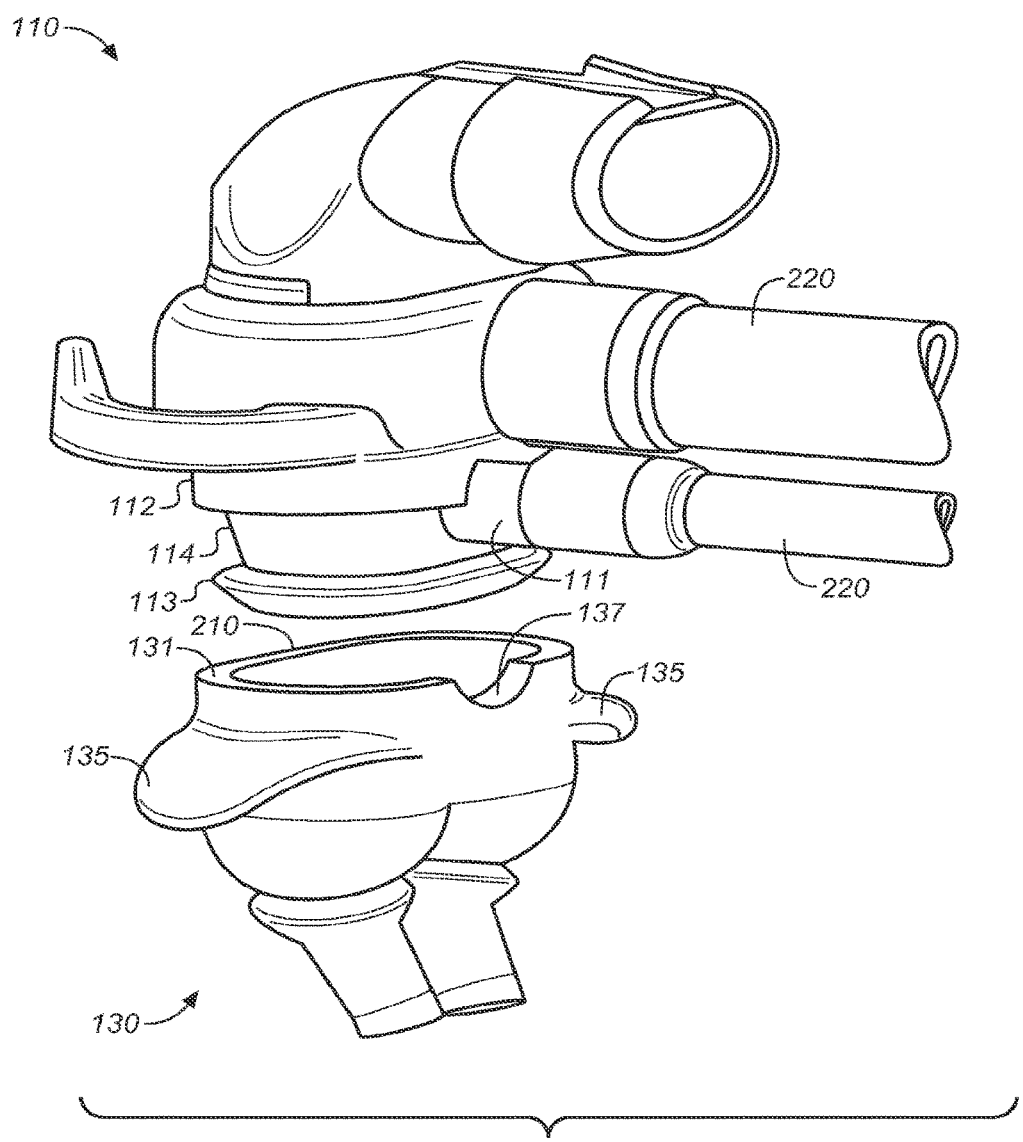
FIG. 2 depicts an isographic view of a generator head and a patient nasal interface, according to one embodiment.

FIG. 2 depicts an isographic view of a generator head 110 and a patient nasal interface 130, according to one embodiment. As depicted in FIG. 2, the generator head 110 is coupled to tubes 220 that in turn are coupled, directly or indirectly, to a nasal airway pressure system. There are different types of nasal airway pressure systems. One is continuous positive airway pressure (CPAP) that generates continuous positive airway pressure for the patient. A CPAP that is used with a nasal interface is referred to as a nasal CPAP (nCPAP). Other examples of airway pressure systems include fixed flow, ventilator type systems and variable flow systems.

FIG. 2 illustrates an example of the patient nasal interface 130's alignment feature 137 with respect to the proximal pressure line port 111, according to one embodiment. The proximal pressure line port 111 is an example of an alignment feature associated with the male portion 115 and the alignment feature 137 is an example of an alignment feature 137 associated with the female portion 138. The alignment feature 137, for example, has a shape that approximates the outer surface of the lower side of the proximal pressure line port 111. Therefore, the alignment feature 137 can be used to provide feedback as to whether the patient nasal interface 130 is properly aligned with the generator head 110 upon insertion. For example, the alignment feature 137 may be a notch with an approximate semi-circular concave shape that aligns with a semi-circular convex shape of the lower side of the proximal pressure line port 111. Various embodiments are well suited to other types of shapes for the alignment feature 137 and the proximal pressure line port 111. Various embodiments are well suited for using a different alignment features besides 137 and 111. Further, various embodiments are well suited for the alignment features 137 and 111 to have other shapes.

Figure 3A:
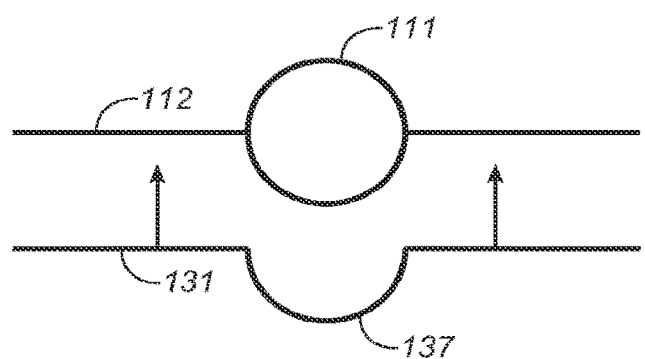
FIG. 3A depicts an exploded view of an example of the patient nasal interface's alignment feature with respect to the proximal pressure line port, according to one embodiment.

FIG. 3A depicts an exploded view of examples of the patient nasal interface 130's alignment feature 137 with respect to the proximal pressure line port 111, according to one embodiment. When the male portion 115 of the generator head 110 is inserted into the patient nasal interface 130's female portion 138, as indicated by the arrows in FIG. 3A, the respective lips 112, 131 will move toward each other as well as the outer surfaces of the alignment feature 137 and the proximal pressure line port 111.

Returning to FIG. 2, the patient nasal interface 130 has an interference feature 210 that indicates to an operator that the patient nasal interface 130 is not properly aligned with the generator head 110 upon insertion 150. According to one embodiment, the interference feature 210 is located toward the front of the patient nasal interface 130 and the alignment feature 137 is located toward the rear of the patient nasal interface 130. According to one embodiment, the interference feature 210 is a tab of material that sticks up from the lip 131. According to one embodiment, other types of features or shapes can be used besides a tab as an interference feature. According to one embodiment, the interface 130's Hp 131 serves as an interference feature.

Figure 3B:
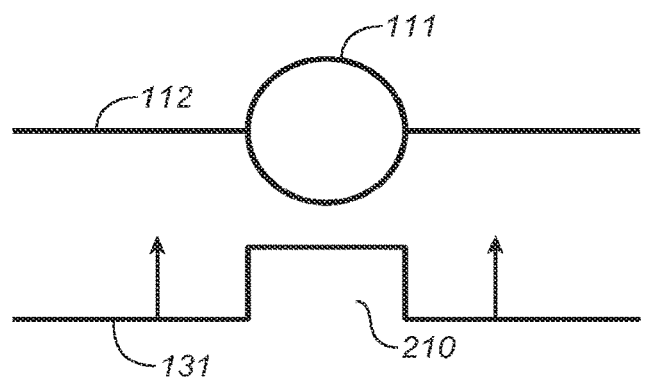
FIG. 3B depicts an exploded view of an example of the patient nasal interface's interference feature with respect to the proximal pressure line port, according to one embodiment.
Figure 3C:
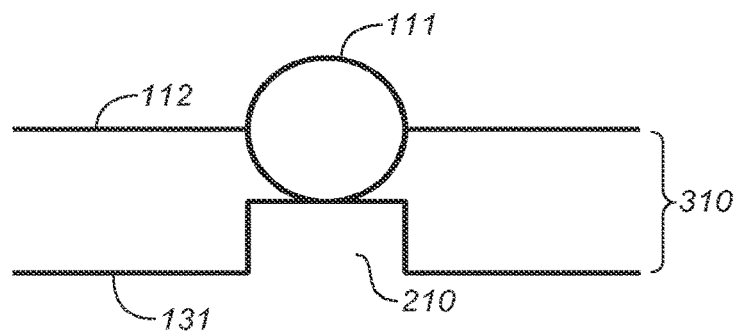
FIG. 3C depicts the lower side of the proximal pressure line port coming into contact with the interference feature causing a noticeable gap between the generator head and the patient nasal interface, according to one embodiment.

FIG. 3B depicts an exploded view of an example of the patient nasal interface 130's interference feature 210 with respect to the proximal pressure line port 111, according to one embodiment. For example, if the patient nasal interface 130 is rotated so that the alignment feature 137 does not align with the lower side of the proximal pressure line port 111, the lower side of the proximal pressure line port 111 will come into contact with the interference feature 210 causing a noticeable gap 310, as depicted in FIG. 3C, between the generator head 110 and the patient nasal interface 130.

The noticeable gap 310, according to one embodiment, provides tactile feedback to the operator performing the insertion that the generator head 110 and the patient nasal interface 130 are not properly aligned. The gap 310 would typically result in a relatively large leak. A relatively large leak, as well as the gap 310, could signal to the operator that there is a problem and could assist the operator in determining where the problem is located.

In contrast, conventional generator heads and patient nasal interfaces may have only a small gap or no gap when they are misaligned, making it difficult for the operator to determine that there is a leak or where the leak is located. Therefore, a typical response is for an operator to tighten a conventional nasal interface to the patient's face, which could lead to skin irritation or skin damage, among other things.

Figure 4:
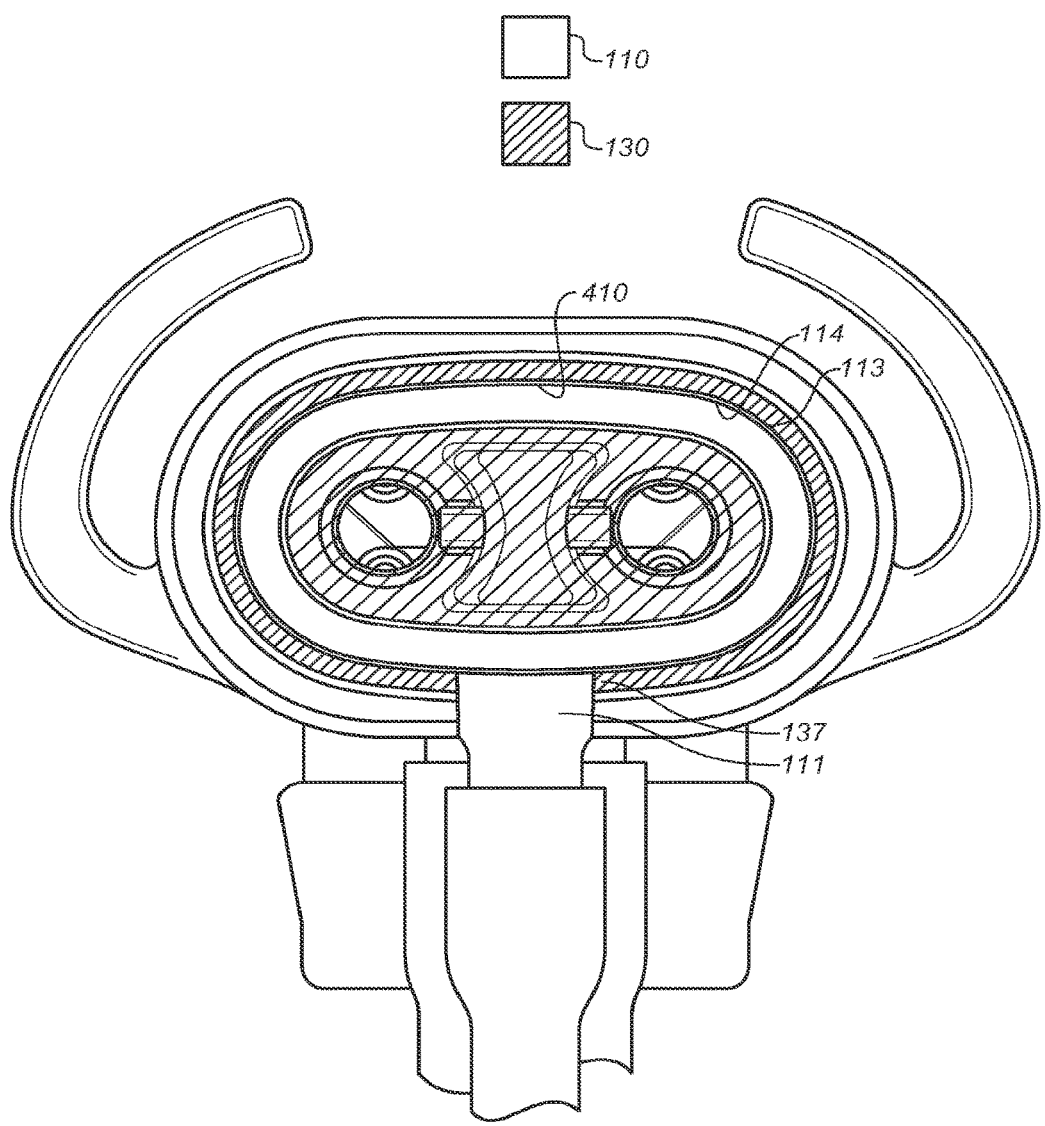
FIG. 4 depicts a bottom view of the generator head inserted into the patient nasal interface, according to one embodiment.

FIG. 4 depicts a bottom view of the generator head 110 inserted into the patient nasal interface 130, according to one embodiment. The patient nasal interface 130 is depicted with hatch marks and the generator head 110 is depicted without hatch marks.

FIG. 4 depicts a sealing circumference 410 between the female portion 138 and the male portion 115. The sealing circumference 410, according to one embodiment, encompasses the entire circumference around and between the male portion 115 and the female portion 138. According to one embodiment, a radial seal is formed at the sealing circumference 410. For example, as discussed herein, the respective external mount 113 and the internal notch 134 are configured to form a radial seal with respect to each other, according to one embodiment. According to one embodiment, the radial seal is formed at the sealing circumference 410.

When the male portion 115 is properly inserted into the female portion 138, a seal is created between the generator head 110 and the patient nasal interface 130 at the respective sealing areas 116, 139 along the sealing circumference 410, according to one embodiment. For example, when properly inserted, the seal prevents air from leaking between the generator head 110's male portion 115 and the patient nasal interface 130's female portion 138.

Figure 5:
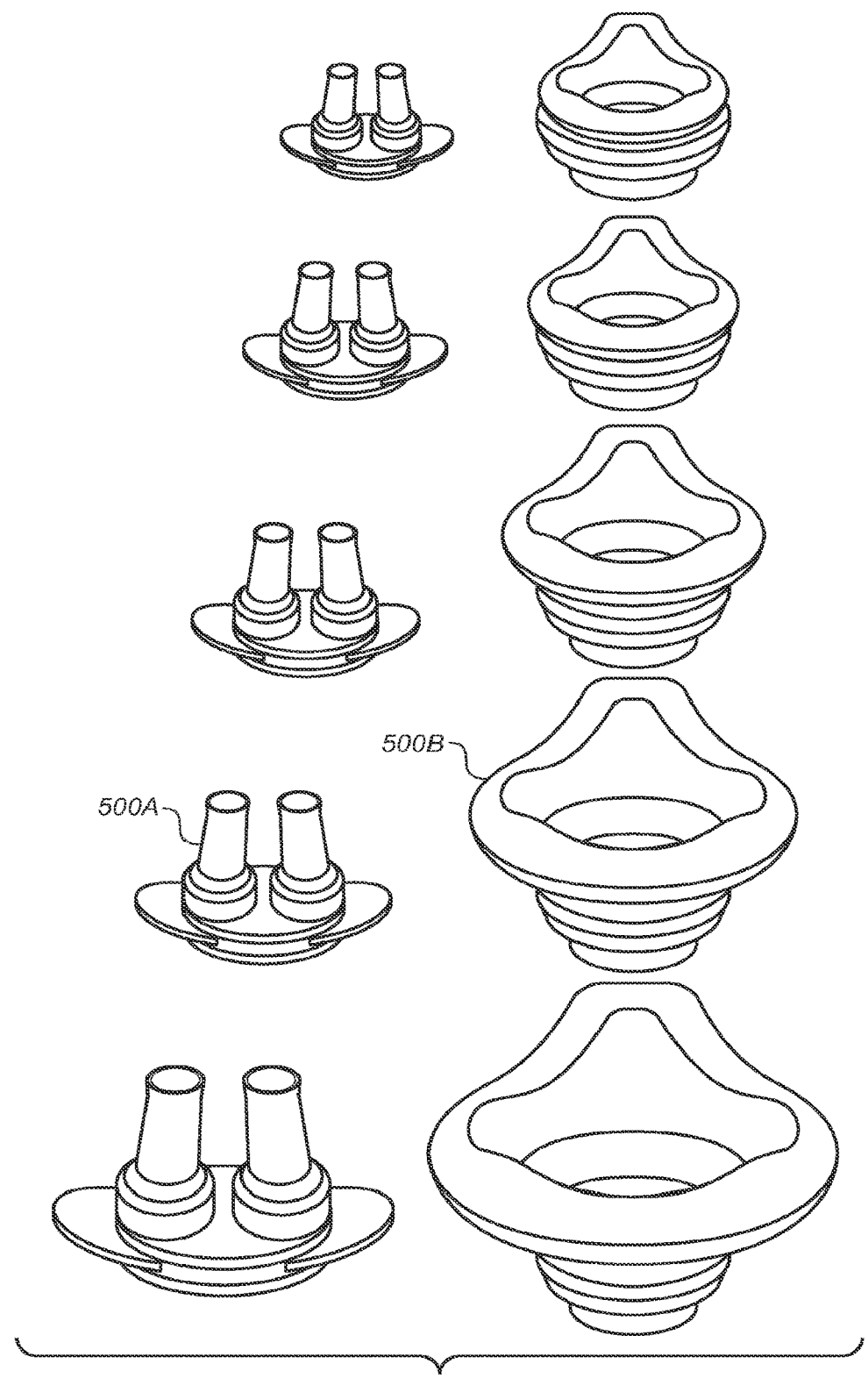
FIG. 5 depicts examples of patient nasal interfaces, according to various embodiments.

FIG. 5 depicts examples of patient nasal interfaces 130, according to various embodiments. FIG. 5 depicts two types of patient nasal interfaces 130, which are prong type 500A and mask type 500B. The prong type 500A typically includes two prongs that can be inserted into the patient's nostrils. The mask type 500B typically includes a cup shaped structure that can cover the person's nose.

Various embodiments are well suited to different sizes of patient nasal interfaces 130. For example, FIG. 5 depicts 5 sizes of patient nasal interfaces 130 for each of the two types 500A, 500B. According to various embodiments, a generator head 110 can be coupled with any size of patient nasal interface 130.

The size of the patient nasal interface 130 can be indicated on the interface 130. For example, an indication of the size can be printed on a tab 135 of a prong type 500A or on the side of a mask type 500B, among other things. The interfaces 130 can be color coded so that each size has its own color.

Conventional patient nasal interfaces may have a plastic shroud that comes close to the patient's face. The plastic shroud is made of a relatively hard plastic and can irritate or damage the patient's skin. According to one embodiment, a plastic shroud that is in proximity of the patient's face is not required. Instead, various embodiments provide for the softer silicone or silicon like material of the patient nasal interface 130 to be in proximity of the patient's face.

Various embodiments provide for the softer silicone or silicon like material of the patient nasal interface 130 to be in proximity of the patient's face instead of a plastic shroud. This provides for a significant reduction in the amount of material used in manufacturing the patient nasal interface 130. According to one embodiment, a patient nasal interface 130 is provided that is approximately 60 percent of the weight of a conventional patient nasal interface. The reduction in the amount of material reduces the cost of manufacturing the patient nasal interfaces 130.

Therefore, a patient nasal interface 130 and a generator head 110, according to various embodiments, provide for reduced possibility of air leaks, feedback indicating proper insertion, feedback indicating proper alignment, ease of use, especially in darkened environments, easier determination of the cause of a leak, reduction in the possibility of skin irritation or skin damage, reduction in the possibility of damage to the nasal septum, reduction in the possibility of patient death, and reduction in cost due to a reduction in the amount of material used in manufacturing, among other things.

Although various embodiments have been described in the context of a patient, for example, in a hospital, various embodiments are well suited for use in other contexts, such as at home or at a sleep clinic.

Although various embodiments have been described in the context of an infant with under developed lungs, various embodiments are well suited for other uses, such as for treatment of sleep apnea.

Various embodiments have been described in the context of registration features 113, 134 that run along the enter circumference of the respective male portion 115 and female portion 138. However, various embodiments are well suited to registration features that are located on a subset of the respective circumferences of the male portion and the female portion. Further, various embodiments are well suited to more than one registration feature being located along the same circumference. For example, there may be a series of smaller registration features that are located along a circumference of the male portion that correspond to a series of smaller registration features that are located along a circumference of the female portion. Since, according to one embodiment, the female portion can wrap around and over the male portion, various embodiments are still well suited to provide a seal that prevents air from leaking between the female portion and the male portion.

According to one embodiment, the lip 131 of the patient nasal interface 130 is not inserted into a groove or any portion of the generator head. According to one embodiment, the generator head 110 does not have and does not require a female portion and the patient nasal interface 130 does not have and does not require a male portion. According to one embodiment, the lip 131 of the patient nasal interface 130 does not require insertion into a groove or any portion of the generator head as a part of coupling. According to one embodiment, the patient nasal interface 130 does not have and does not require a flange that projects horizontally from the top of the patient nasal interface 130's lip 131.

Examples of the subject matter are thus described. Although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the claims.

Various embodiments have been described in various combinations. However, any two or more embodiments may be combined. Further, any embodiment may be used separately from any other embodiment. Features, structures, or characteristics of any embodiment may be combined in any suitable manner with one or more other features, structures, or characteristics.

What is claimed is:

1. A nasal airway pressure system, comprising:
  a generator head configured to receive air for delivery to a patient, the generator head comprising:
    an internal surface that defines an internal cavity configured to allow airflow therethrough, and
    an outer surface having a notch disposed between a lip and a convex external mount; and
  a disposable patient nasal interface configured to couple to the generator head to provide airflow from the generator head to the patient, the disposable patient nasal interface comprising:
    an internal surface that is configured to engage the outer surface of the generator head when the disposable patient nasal interface is coupled to the generator head, wherein the internal surface of the disposable patient nasal interface comprises a concave internal notch configured to receive the convex external mount of the generator head for coupling of the disposable patient nasal interface to the generator head.

2. The nasal airway pressure system of claim 1, wherein the internal surface of the disposable patient nasal interface further comprises a slanted wall disposed between a lip of the disposable patient nasal interface and the concave internal notch, wherein the slanted wall approximates a shape of the notch of the outer surface of the generator head.

3. The nasal airway pressure system of claim 2, wherein the slanted wall has a larger circumference at the lip of the disposable patient nasal interface than toward the concave internal notch.

4. The nasal airway pressure system of claim 2, wherein the disposable patient nasal interface further comprises a pair of prongs configured to be inserted into nostrils of the patient.

5. The nasal airway pressure system of claim 2, wherein the disposable patient nasal interface further comprises an external notch that extends from the lip of the disposable patient nasal interface into a base of the disposable patient nasal interface toward the concave internal notch.

6. The nasal airway pressure system of claim 5, wherein the generator head further comprises a port and wherein the external notch of the disposable patient nasal interface is configured to receive at least a portion of the port of the generator head to align the disposable patient nasal interface with the generator head.

7. The nasal airway pressure system of claim 1, wherein the concave internal notch of the disposable patient nasal interface is a triangular notch and wherein the convex external mount of the generator head is a corresponding triangular protrusion.

8. The nasal airway pressure system of claim 1, wherein the concave internal notch of the disposable patient nasal interface is a semi-circular notch and wherein the convex external mount of the generator head is a corresponding semi-circular protrusion.

9. The nasal airway pressure system of claim 1, wherein the disposable patient nasal interface is formed from a material that stretches to conform to the generator head upon insertion of the convex external mount into the concave internal notch, and wherein when the generator head and the disposable patient nasal interface are in an attached configuration in which the generator head is inserted into and received by the disposable patient nasal interface:
   the lips of both the generator head and the disposable patient nasal interface engage,
   the internal notch of the disposable patient nasal interface engages with the external mount of the generator head, and
   a slanted wall between the lip and the external mount of the generator head engages with a slanted wall between the lip and the internal notch of the disposable patient nasal interface to form an interference fitment between the generator head and the disposable patient nasal interface.

10. The nasal airway pressure system of claim 9, wherein the material of the disposable patient nasal interface allows the convex external mount to press into the material.

11. The nasal airway pressure system of claim 1, wherein the convex external mount and the concave internal notch are configured to provide a snap when the convex external mount pops into place inside of the concave internal notch.

12. A generator head for a nasal airway pressure system, the generator head comprising:
   an internal surface that defines an internal cavity configured to allow airflow therethrough, and
   an outer surface, comprising:
      a notch;
      a lip; and
      a convex external mount, wherein the notch is disposed between the lip and the convex external mount.

13. The generator head of claim 12, further comprising a port that extends through at least a portion of the notch.

14. The generator head of claim 12, wherein the convex external mount has a shape that approximates the shape of a corresponding internal notch of a patient nasal interface of the nasal airway pressure system.

15. The generator head of claim 14, wherein the convex external mount is configured to provide a snap when the convex external mount pops into place inside of the internal notch of the patient nasal interface.

16. A patient nasal interface for a nasal airway pressure system, the patient nasal interface comprising:
   a lip;
   an internal surface extending from the lip, the internal surface configured to engage an outer surface of a generator head of the nasal airway pressure system, wherein the internal surface comprises:
   a concave internal notch; and
   a slanted wall extending from the lip toward the concave internal notch, wherein the slanted wall has a larger circumference at the lip than toward the concave internal notch.

17. The patient nasal interface of claim 16, wherein the slanted wall approximates a shape of a notch of an outer surface of the generator head.

18. The patient nasal interface of claim 17, wherein the concave internal notch is configured to receive a convex external mount of the generator head for coupling of the patient nasal interface to the generator head.

19. The patient nasal interface of claim 16, further comprising two prongs, disposed opposite the lip and configured to be inserted into nostrils of a patient.

20. The patient nasal interface of claim 16, further comprising an external notch that extends from the lip into a base of the patient nasal interface toward the concave internal notch.

\* \* \* \* \*